US011369330B2

(12) United States Patent
Kaneko et al.

(10) Patent No.: US 11,369,330 B2
(45) Date of Patent: Jun. 28, 2022

(54) X-RAY DIAGNOSIS APPARATUS

(71) Applicant: Canon Medical Systems Corporation, Otawara (JP)

(72) Inventors: Makoto Kaneko, Otawara (JP); Koutaro Matsuo, Otawara (JP); Ko Fuchigami, Otawara (JP); Hajime Yoshida, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 174 days.

(21) Appl. No.: 15/946,819

(22) Filed: Apr. 6, 2018

(65) Prior Publication Data
US 2018/0333124 A1 Nov. 22, 2018

(30) Foreign Application Priority Data

May 16, 2017 (JP) .............................. JP2017-097374
Apr. 4, 2018 (JP) .............................. JP2018-072276

(51) Int. Cl.
A61B 6/00 (2006.01)
A61B 6/06 (2006.01)
A61B 6/10 (2006.01)

(52) U.S. Cl.
CPC .............. A61B 6/5235 (2013.01); A61B 6/06 (2013.01); A61B 6/107 (2013.01); A61B 6/4035 (2013.01);
(Continued)

(58) Field of Classification Search
CPC ......... A61B 6/06; A61B 6/107; A61B 6/4035; A61B 6/4441; A61B 6/463; A61B 6/469;
(Continued)

(56) References Cited

U.S. PATENT DOCUMENTS 6,282,261 B1 * 8/2001 Mazess ................ A61B 6/4225
348/E5.088
9,480,437 B2 * 11/2016 Watanabe ................ A61B 6/06
(Continued)

FOREIGN PATENT DOCUMENTS

JP 10-234714 9/1998
JP 2005-27823 2/2005
(Continued)

OTHER PUBLICATIONS

Office Action dated Feb. 15, 2022 in Japanese Application No. 2018-072276.

Primary Examiner — Dani Fox
Assistant Examiner — Soorena Kefayati
(74) Attorney, Agent, or Firm — Oblon, McClelland, Maier & Neustadt, L.L.P.

(57) ABSTRACT

According to one embodiment, the X-ray diagnosis apparatus includes an X-ray detector, X-ray diaphragm apparatus, and processing circuitry controlling the X-ray diaphragm apparatus to shield the X-rays from passing through a X-ray filter outside an aperture region or a partial region during a transition from first fluoroscopy employing an X-ray filter to second fluoroscopy employing diaphragm blades, generating a first and second fluoroscopic image during the first and second fluoroscopy respectively, generating a composite image during the second fluoroscopy by combining a non-ROI image of the first fluoroscopic image and a ROI image of the second fluoroscopic image, and displaying the first fluoroscopic image and the composite image on the display during the first and second fluoroscopy respectively.

11 Claims, 9 Drawing Sheets

(52) U.S. Cl.
CPC .............. *A61B 6/463* (2013.01); *A61B 6/469* (2013.01); *A61B 6/487* (2013.01); *A61B 6/542* (2013.01); *A61B 6/545* (2013.01); *A61B 6/4441* (2013.01)

(58) Field of Classification Search
CPC ....... A61B 6/487; A61B 6/5235; A61B 6/542; A61B 6/545
See application file for complete search history.

(56) References Cited

U.S. PATENT DOCUMENTS

| | | | | |
|---|---|---|---|---|
| 10,278,667 B2* | 5/2019 | Iijima | .................. | A61B 6/5258 |
| 2007/0116171 A1* | 5/2007 | Hsieh | .................... | A61B 6/488 |
| | | | | 378/8 |
| 2011/0038517 A1* | 2/2011 | Mistretta | ................ | A61B 6/485 |
| | | | | 382/128 |
| 2013/0012813 A1* | 1/2013 | Sakaguchi | ............... | A61B 6/12 |
| | | | | 600/431 |
| 2013/0101084 A1* | 4/2013 | Shimizu | ................. | A61B 6/487 |
| | | | | 378/42 |
| 2013/0129255 A1* | 5/2013 | Homma | ................. | A61B 6/487 |
| | | | | 382/294 |
| 2013/0136332 A1* | 5/2013 | Uehara | ................. | G06T 7/0012 |
| | | | | 382/132 |
| 2013/0315370 A1* | 11/2013 | Watanabe | .............. | A61B 6/542 |
| | | | | 378/42 |
| 2013/0336552 A1* | 12/2013 | Sehnert | .................. | A61B 6/487 |
| | | | | 382/128 |
| 2014/0169525 A1* | 6/2014 | Shimizu | ................. | A61B 6/542 |
| | | | | 378/62 |
| 2014/0328462 A1* | 11/2014 | Uehara | ................. | A61B 6/5288 |
| | | | | 378/62 |
| 2014/0341350 A1* | 11/2014 | Muroi | .................... | A61B 6/504 |
| | | | | 378/62 |
| 2015/0078516 A1* | 3/2015 | Ohashi | ................. | A61B 6/4042 |
| | | | | 378/42 |
| 2015/0272520 A1* | 10/2015 | Kobayashi | ........... | A61B 6/4035 |
| | | | | 378/62 |
| 2015/0272533 A1* | 10/2015 | Totsuka | .................. | A61B 6/06 |
| | | | | 378/62 |
| 2016/0029989 A1* | 2/2016 | Nagae | .................... | A61B 6/469 |
| | | | | 378/42 |
| 2016/0078621 A1* | 3/2016 | Nagae | .................... | A61B 6/507 |
| | | | | 382/130 |
| 2016/0143605 A1* | 5/2016 | Nagae | .................... | A61B 6/487 |
| | | | | 382/103 |
| 2016/0350913 A1* | 12/2016 | Nagae | .................... | G06T 7/174 |
| 2017/0112456 A1* | 4/2017 | Ohga | .................... | A61B 6/587 |
| 2018/0021000 A1* | 1/2018 | Akiyama | ................ | A61B 6/06 |
| | | | | 378/62 |
| 2021/0307705 A1* | 10/2021 | Kim | ....................... | A61B 6/145 |

FOREIGN PATENT DOCUMENTS

| | | |
|---|---|---|
| JP | 2006-288554 | 10/2006 |
| JP | 2007-59233 | 3/2007 |
| JP | 2007-159913 | 6/2007 |
| JP | 2012-75782 | 4/2012 |
| JP | 2013-90912 | 5/2013 |
| JP | 2014-144053 | 8/2014 |
| JP | 2015-198783 | 11/2015 |
| JP | 2015-211914 | 11/2015 |
| JP | 2016-101335 | 6/2016 |

* cited by examiner

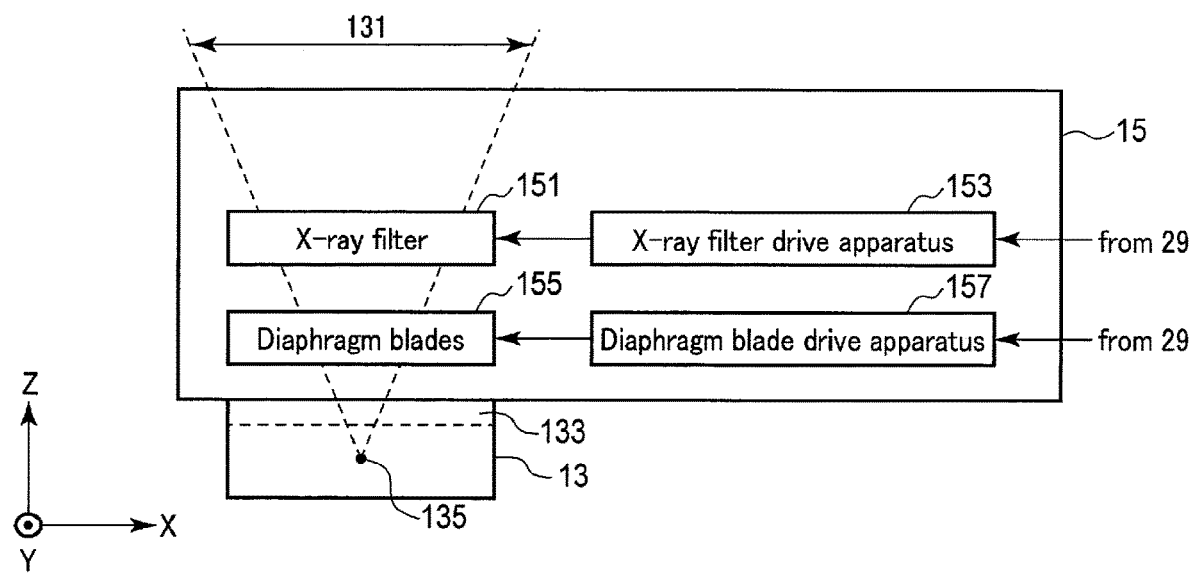
F I G. 2
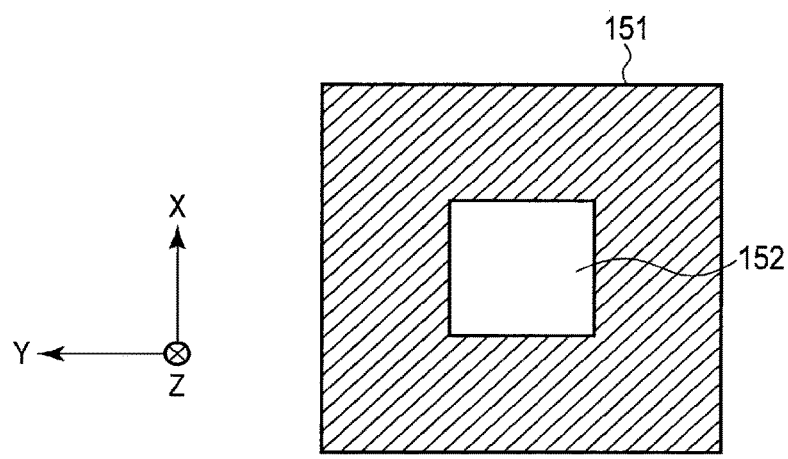
F I G. 3

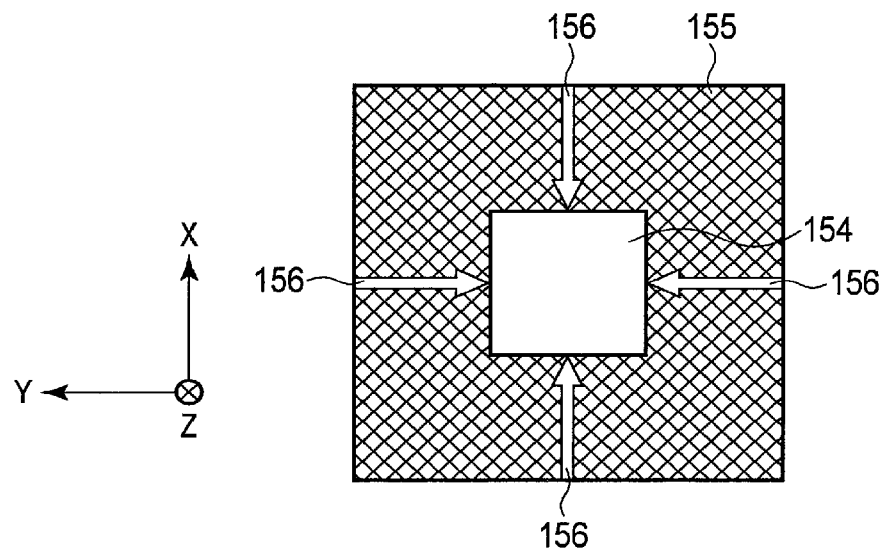
F I G. 4
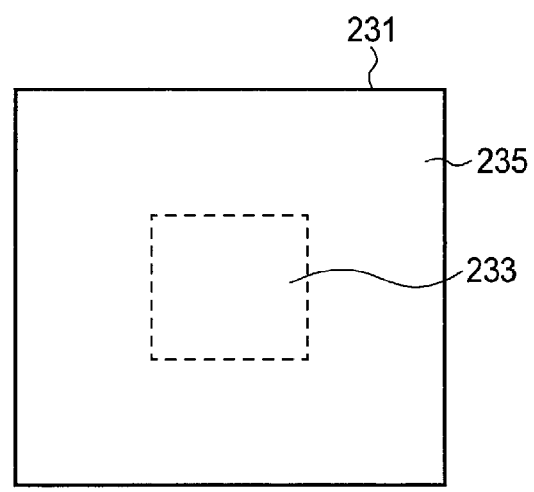
F I G. 5

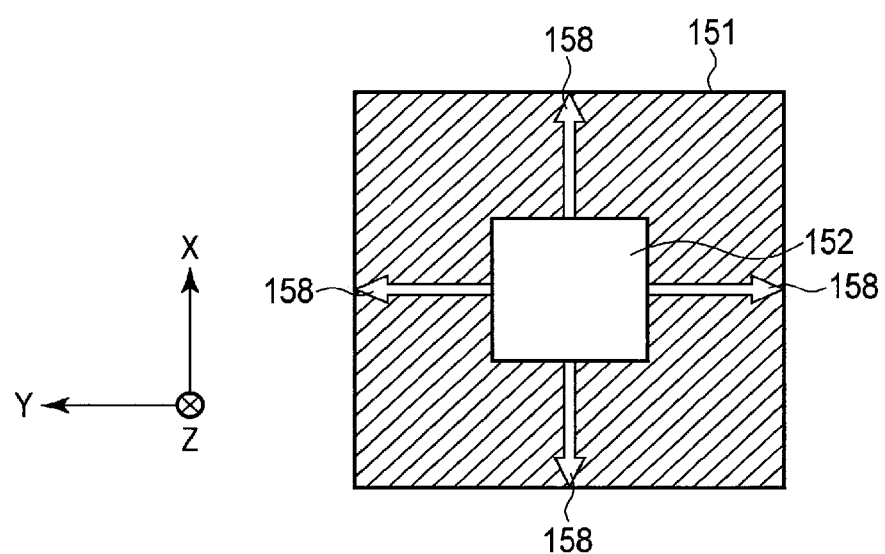
F I G. 7

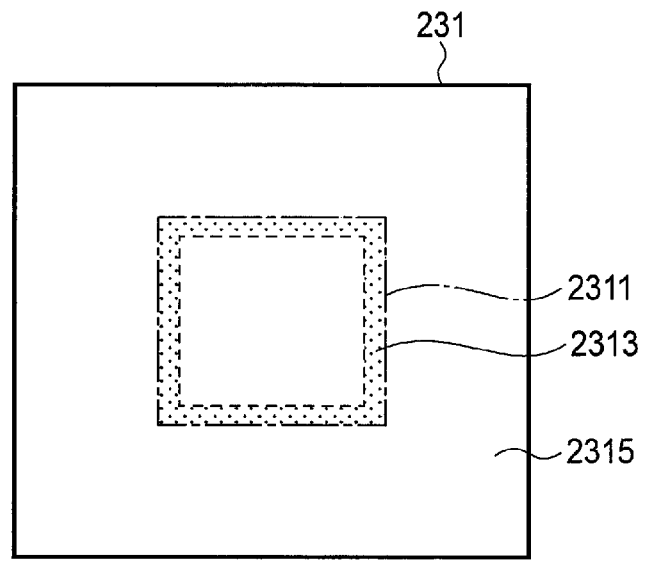
F I G. 10
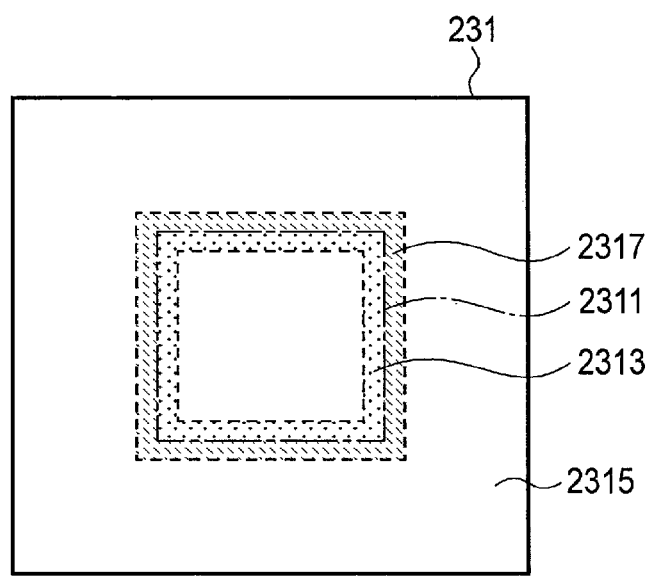
F I G. 11

X-RAY DIAGNOSIS APPARATUS

CROSS-REFERENCE TO RELATED APPLICATIONS

This application is based upon and claims the benefit of priority from the prior Japanese Patent Applications No. 2017-097374, filed May 16, 2017; and No. 2018-072276, filed Apr. 4, 2018, the entire contents of all of which are incorporated herein by reference.

FIELD

Embodiments described herein relate generally to an X-ray diagnosis apparatus.

BACKGROUND

In an X-ray circulatory diagnosis apparatus, an X-ray filter arranged on the periphery portion of a Region of Interest (hereinafter referred to as "ROI") may be adopted for radiation dose reduction to offer fluoroscopy that provides a real-time image (hereinafter referred to as "ROI fluoroscopy"). With such fluoroscopy, if the X-ray filter is to reduce the dose by 1/10 and the ratio of the ROI to the entire area of the X-ray irradiation range is 1/9, the X-ray dose in the ROI fluoroscopy can be reduced by 1/5 (1/9×1+1/9×1/10×8) in comparison with the entire X-ray irradiation range being irradiated without an X-ray filter. On the other hand, in the X-ray circulatory diagnosis apparatus, the range corresponding to a non-region of interest (non-ROI) with respect to the entire X-ray irradiation range may be defined by diaphragm blades to offer the fluoroscopy that provides a real-time image (hereinafter, referred to as spot fluoroscopy).

With the spot fluoroscopy, the X-ray dose can be reduced by 1/9 (=1/9×1+1/9×0) in comparison with the entire X-ray irradiation range being irradiated without an X-ray filter. This means that the X-ray dose reduction in the ROI fluoroscopy is approximately one half of the X-ray dose reduction in the spot fluoroscopy. Although the spot fluoroscopy exhibits an excellent dose reduction in comparison with the ROI fluoroscopy, the spot fluoroscopy does not include any image information for the ROI peripheral portion.

BRIEF DESCRIPTION OF THE DRAWINGS

FIG. 2 is a diagram showing an example structure of an X-ray diaphragm apparatus according to the present embodiment.

FIG. 3 is a diagram of an X-ray irradiation range during ROI fluoroscopy when viewed from an X-ray irradiation window side according to the present embodiment.

FIG. 4 is a diagram of an X-ray irradiation range during spot fluoroscopy when viewed from the X-ray irradiation window side according to the present embodiment.

FIG. 5 is a diagram showing an example of a composite image according to the present embodiment.

FIG. 7 is a diagram showing an X-ray irradiation range after a transition from the spot fluoroscopy to the ROI fluoroscopy, when viewed from the X-ray irradiation window side according to the present embodiment.

FIG. 10 is a diagram showing an example of a ROI, the periphery portion of the ROI, and a non-ROI in a composite image according to the second modification of the present embodiment.

FIG. 11 is a diagram showing an example of the composite image including a ROI, a periphery portion of the ROI, and a periphery portion of the non-ROI that is adjacent to the periphery portion of the ROI according to the third modification of the present embodiment.

DETAILED DESCRIPTION

Figure 1:
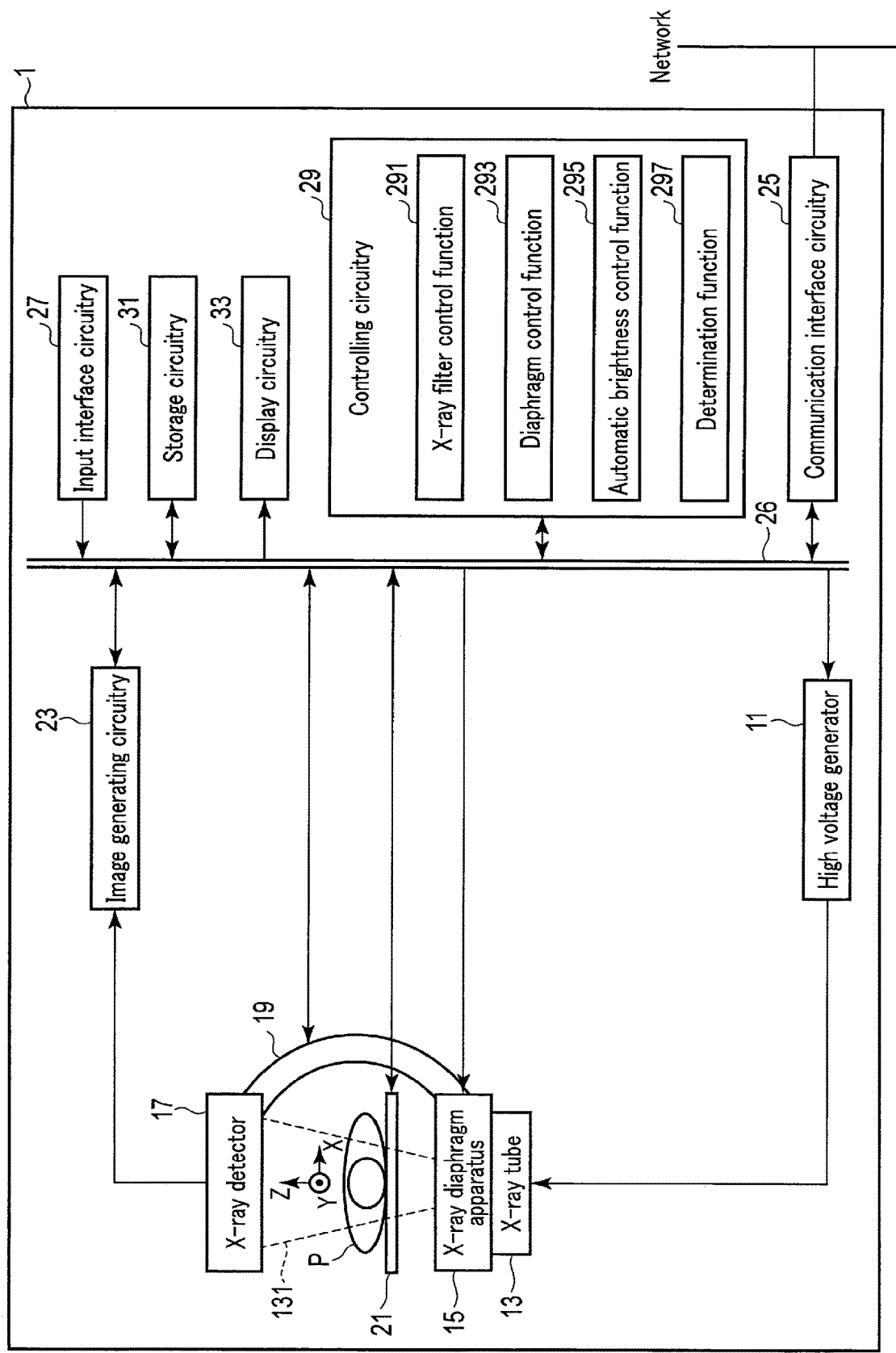
FIG. 1 is a diagram showing the structure of an X-ray diagnosis apparatus according to the present embodiment.

According to one embodiment, an X-ray diagnosis apparatus includes an X-ray detector, an X-ray diaphragm apparatus, and processing circuitry.

The X-ray detector faces the X-ray tube that generates X-rays to detect the X-rays.

The X-ray diaphragm apparatus includes an X-ray filter and diaphragm blades. The X-ray filter includes either a partial region having a larger X-ray transmissivity than the remaining region of the X-ray filter or an aperture region. The diaphragm blades shield the X-rays.

The processing circuitry controls the X-ray diaphragm apparatus shield the X-rays from passing through the X-ray filter outside the aperture region or the partial region during a transition from first fluoroscopy employing the X-ray filter to second fluoroscopy employing the diaphragm blades to restrict an irradiation range. The processing circuitry generates a first fluoroscopic image based on the output from the X-ray detector during the first fluoroscopy. The processing circuitry also generates a second fluoroscopic image based on the output from the X-ray detector during the second fluoroscopy. Thereafter, the processing circuitry generates a composite image during the second fluoroscopy, by combining a non-region-of-interest image of the first fluoroscopic image and a region-of-interest image of the second fluoroscopic image. The non-region-of-interest image corresponds to an irradiation region of X-rays that have passed outside the aperture region or the partial region. The region-of-interest image corresponds to an irradiation region of the X-rays that have passed through the aperture region or the partial region. The processing circuitry displays the first fluoroscopic image on a display during the first fluoroscopy. The processing circuitry displays the composite image on the display during the second fluoroscopy.

The purpose is to achieve, during the spot fluoroscopy, the reduction in dose corresponding to the spot fluoroscopy and to offer an X-ray diagnosis apparatus that can display an image of the ROI peripheral portion.

The X-ray diagnosis apparatus according to the present embodiment will be explained with reference to the drawings. In the following explanation, structural components having substantially the same functions or structures are given the same reference numerals, and the explanation may be repeated only where it is necessary.

FIG. 1 is a diagram showing the structure of an X-ray diagnosis apparatus 1 according to the present embodiment. The X-ray diagnosis apparatus 1 includes a high voltage generator 11; an X-ray tube 13; an X-ray diaphragm apparatus 15; an X-ray detector 17, a support frame 19; a bed having a table top 21, which is not shown; image generating circuitry (image generating unit) 23; communication interface circuitry 25; input interface circuitry (input unit) 27; controlling circuitry (controller) 29; storage circuitry (storage unit) 31; and display circuitry (display unit) 33.

Figure 12:
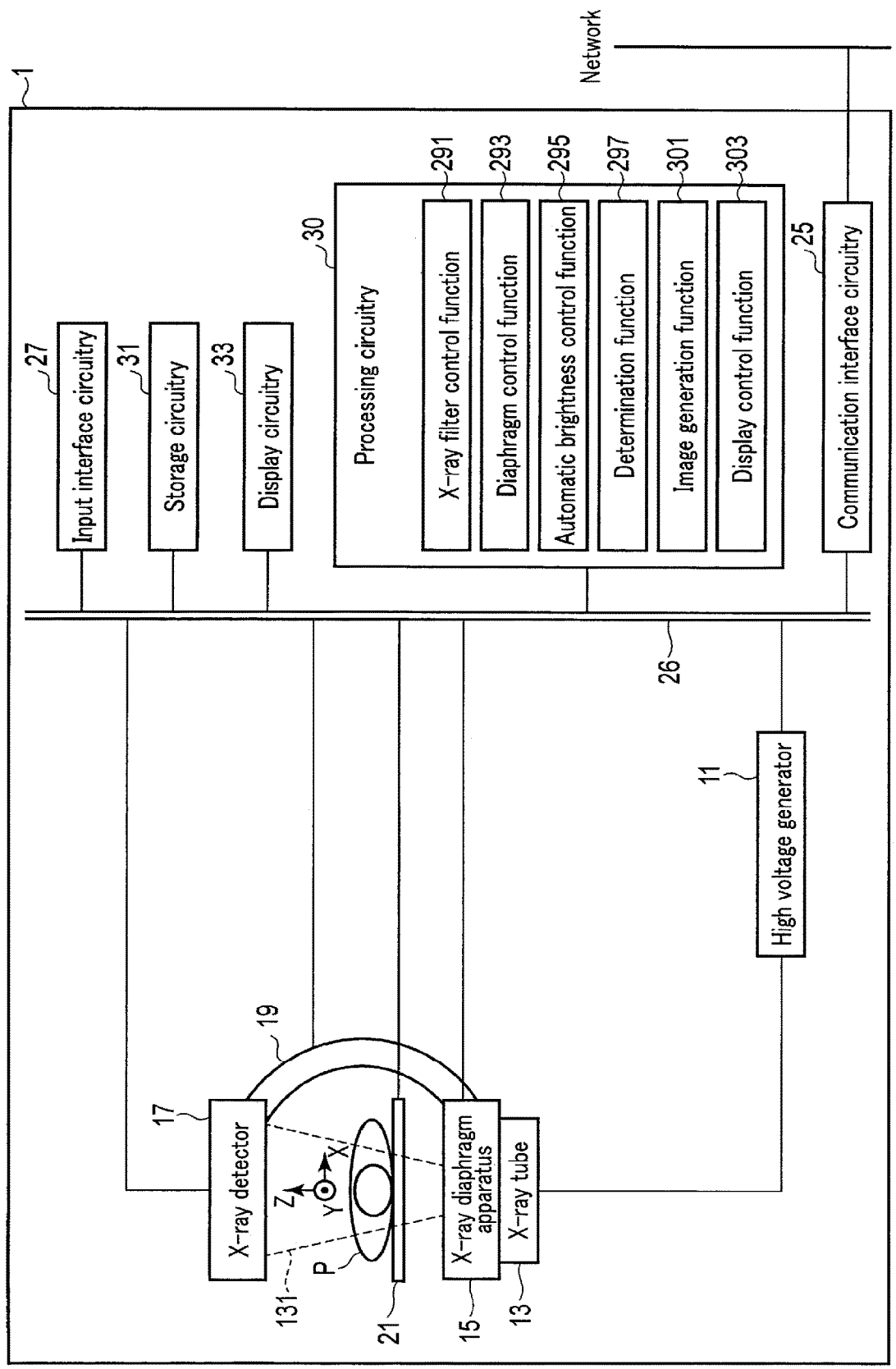
FIG. 12 is a diagram showing a modification example of the structure according to the present embodiment.

Alternatively, the X-ray diagnosis apparatus 1 according to the present embodiment may be configured as illustrated in FIG. 12. FIG. 12 is a diagram showing a modification example structure according to the present embodiment. The X-ray diagnosis apparatus 1 includes a high voltage generator 11; an X-ray tube 13; an X-ray diaphragm apparatus 15; an X-ray detector 17; a support frame 19; a bed having a table top 21, which is not shown; communication interface circuitry 25; input interface circuitry (input unit) 27; processing circuitry (processing unit) 30; storage circuitry (storage unit) 31; and display circuitry (display unit) 33. The processing circuitry 30 in FIG. 12 corresponds to the controlling circuitry 29 in FIG. 1. In other words, the various processes and operations performed at the processing circuitry 30 include the processes and operations performed at the controlling circuitry 29. In the following explanation, the processing circuitry 30 may be understood from the description of the "controlling circuitry 29" by replacing this circuitry with the "processing circuitry 30". The image generation function (image generator) 301 of the processing circuitry 30 is provided with a function of implementing various processes and operations performed at the image generating circuitry 23 in FIG. 1. The image generation function 301 therefore may be understood from the description of the "image generating circuitry 23" by replacing this circuitry with the "image generation function 301 of the processing circuitry 30".

The high voltage generator 11 generates a tube current to be supplied to the X-ray tube 13, and a tube voltage (high voltage) to be applied to the X-ray tube 13. The high voltage generator 11 supplies to the X-ray tube 13 tube currents suitable for the X-ray imaging and for the X-ray fluoroscoping in accordance with the X-ray irradiation conditions, which will be described later, under the control of the controlling circuitry 29. The high voltage generator 11 also applies to the X-ray tube 13 tube voltages suitable for the X-ray imaging and for the X-ray fluoroscoping in accordance with the X-ray irradiation conditions, under the control of the controlling circuitry 29.

The X-ray irradiation conditions may include, for example, a tube current, tube voltage, irradiation time length, and the product of the tube current (mA) and irradiation time length (s) (hereinafter referred to as a tube current-time product (mAs)), for each X-ray irradiation. The tube voltage may be applied by the high voltage generator 11 by continuously applying a tube voltage to the X-ray tube 13 (hereinafter referred to as high voltage pulse application) or by applying high voltage pulses to the X-ray tube 13 through high voltage switching (hereinafter referred to as high voltage pulse application). In the description below, the high voltage generator 11 that adopts the high voltage pulse application for X-ray fluoroscopy will be explained.

The X-ray tube 13 emits X-rays from the X-ray focal spot (hereinafter referred to as a "tube focal spot") based on the tube current supplied by the high voltage generator 11 and the tube voltage applied by the high voltage generator 11. The X-rays emitted from the tube focal spot are applied to a subject P with a non-target area shielded by the X-ray diaphragm apparatus 15. The X-ray irradiation range 131 is indicated by dashed lines. In this explanation, the X-ray tube 13 according to the present embodiment is of a rotating anode type. The X-ray tube 13 according to the present embodiment, however, may be of a fixed anode type or any other type. The X-ray tube 13 emits discrete X-ray pulses at specific time intervals in accordance with the application of high voltage pulses generated by high voltage switching. A lead cone is attached to the X-ray irradiation window of the X-ray tube 13 to shield against off-focus X-rays that are emitted out of the tube focus spot.

FIG. 2 is a diagram showing an example structure of the X-ray diaphragm apparatus 15 according to the present embodiment. As illustrated in this drawing, the X-ray diaphragm apparatus 15 includes an X-ray filter 151, an X-ray filter drive apparatus 153 that drives the X-ray filter 151, diaphragm blades 155, and a diaphragm blade drive apparatus 157 that drives the diaphragm blades 155.

The X-ray diaphragm apparatus 15 is provided adjacent to an X-ray irradiation window 133 of the X-ray tube 13 on the front surface of the X-ray tube 13. This X-ray diaphragm apparatus 15 defines the irradiation range of the X-rays emitted from a tube focal spot 135. The X-ray diaphragm apparatus 15 may include, in addition to the X-ray filter 151, various filters (e.g., radiation quality adjustment filter, X-ray added filter, and dose reduction filter). The relative positions of the X-ray filter 151 and diaphragm blades 155 are not limited to the relationship illustrated in FIG. 2. For example, the X-ray filter 151 may be positioned on the side of the tube focal spot 135, and the diaphragm blades 155 may be positioned on the side of the table top.

The X-ray filter 151 has an aperture region to reduce the dose of X-rays passing outside the aperture region. The X-ray filter 151 may be configured in a manner so that the size of the aperture region is adjustable in accordance with the size of the region of interest (ROI) of the subject P in the X-ray irradiation range 131.

Figure 13:
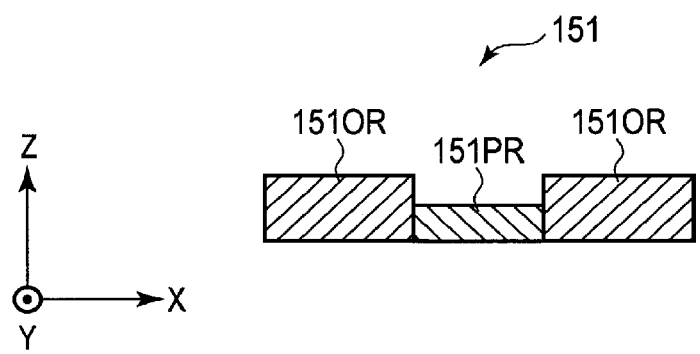
FIG. 13 is a cross section of a different X-ray filter according to the present embodiment.

In place of the aperture region, the X-ray filter 151 may include a region having a greater X-ray transmissivity than the remaining region of the filter. FIG. 13 is a diagram for showing an example of the cross section of an X-ray filter that is different from the aforementioned X-ray filter having the aperture region. As illustrated in this drawing, the X-ray filter 151 includes a partial region 151PR having a greater X-ray transmissivity than the other region 151OR. The X-ray filter 151 reduces larger doses of X-rays passing through the outer region outside the partial region, or in other words the other region 151OR, in comparison with the partial region 151PR. That is, the X-ray diaphragm apparatus 15 according to the present embodiment is provided with an X-ray filter that includes either a partial region having a transmissivity greater than the remaining region of the filter or an aperture region, and diaphragm blades that shield against the X-rays.

The X-ray filter drive apparatus 153 drives the X-ray filter 151 under the control of an X-ray filter control function 291 of the controlling circuitry 29. Specifically, the X-ray filter drive apparatus 153 accomplishes a translational movement of the X-ray filter 151 along the x-axis and y-axis indicated in FIG. 2, employing the X-ray filter control function 291. The X-ray filter drive apparatus 153 further accomplishes the translational movement of the X-ray filter 151 along the z-axis indicated in FIG. 2, employing the X-ray filter control function 291, in accordance with the ROI enlargement instruction or reduction instruction received via the input interface circuitry 27. The X-ray filter drive apparatus 153 may change the size of the aperture region of the X-ray filter 151 employing the X-ray filter control function 291 in accordance with the ROI enlargement instruction or reduction instruction.

The diaphragm blades 155 may be composed of a plurality of blades to shield the X-rays. The diaphragm blades 155 limit the X-ray irradiation range 131 in accordance with the irradiation area of the body surface of the subject P onto which X-rays are applied so as to avoid unnecessary radiation exposure to the X-rays emitted from the tube focal spot 135 in the area that is not an imaging targeted area. The diaphragm blades 155 may include a first set of blades that are movable in the x-axis direction, and a second set of blades that are movable in the y-axis direction. Each of the first and second sets of blades may be formed of lead capable of shielding X-rays. The first and second sets of blades are moved in synchronization by the blade drive apparatus 157. The diaphragm blades 155 are not limited to rectangular blades, but may be polygonal blades or circular blades.

The blade drive apparatus 157 drives the diaphragm blades 155 in accordance with the diaphragm control function 293 of the controlling circuitry 29. With the diaphragm blades 155 that are driven, the X-ray irradiation range 131 changes. For example, the blade drive apparatus 157 drives the diaphragm blades 155 to reduce the X-ray irradiation range 131 to the region of interest. The blade drive apparatus 157 also drives the diaphragm blades 155 to match the X-ray irradiation range 131 with the aperture region or partial region 151PR of the X-ray filter 151.

The X-ray detector 17 is provided to face the X-ray tube 13 to detect the X-rays emitted from the X-ray tube 13. The X-ray detector 17 may be composed, for example, of a flat panel detector (hereinafter referred to as an FPD). This FPD includes a plurality of semiconductor detectors. Alternatively, an image intensifier may be adopted for the X-ray detector 17. The electric signals generated by the semiconductor detectors in response to the X-ray incidence are output to an analog-to-digital converter (hereinafter referred to as an A/D converter) that is not shown. The A/D converter converts the electric signals to digital data. The A/D converter outputs this digital data to the image generating circuitry 23 or processing circuitry 30.

The support frame 19 supports the X-ray tube 13 and X-ray detector 17 in a movable manner. In particular, the support frame 19 is a C-arm. The C-arm carries the X-ray tube 13 and X-ray detector 17 in a manner as to face each other. A support pillar that is not shown supports the C-arm in a slidable manner in a direction along the C shape of the C-arm (hereinafter referred to as the "first direction") by means of a guide rail and linear motion bearing. The support pillar is mounted on the floor of an examination room, and supports the C-arm by means of bearings or the like in a rotatable manner in a direction perpendicular to the first direction (hereinafter referred to as the "second direction"). The support pillar may support the C-arm by means of the bearings in a manner to allow a movement parallel to the directions of the short axis (x-axis) and long axis (y-axis) of the table top 21. Furthermore, the C-arm supports the X-ray tube 13 and X-ray detector 17, for example, by means of the guide rail and linear motion bearing in a manner so that the distance between the tube focal spot 135 of the X-ray tube 13 and the center of the X-ray detector 17 (i.e., source image distance: hereinafter referred to as "SID") is changeable.

In place of the C-arm, an Ω-arm may be adopted as the support frame 19, or two arms (such as robot arms) may be adopted, for example, to separately support the X-ray tube 13 and X-ray detector 17. Furthermore, the support frame 19 may have a biplanar structure including a C-arm and Ω-arm.

The bed (not shown in the drawings) supports the table top 21 (decubitus table) in a movable manner to carry the subject P. The subject P is carried on the table top 21.

The drive apparatus (not shown in the drawings) drives, for example, the support frame 19 and the bed. The drive apparatus may include a motor and a transfer mechanism (e.g., a chain drive, belt drive, and ball screw) to transfer the power generated by the motor to different units that are to be driven. The drive apparatus slides the support frame 19 in the first direction and rotates the support frame 19 in the second direction in accordance with a drive signal corresponding to a control signal received from the controlling circuitry 29. During the X-ray fluoroscoping and X-ray imaging, the subject P is positioned between X-ray tube 13 and X-ray detector 17 on the table top 21. The drive apparatus may rotate the X-ray detector 17 under the control of the controlling circuitry 29 with the SID serving as the rotation axis.

The drive apparatus drives and moves the table top 21 under the control of the controlling circuitry 29. Specifically, the drive apparatus slides the table top 21 in the short axis direction (x-axis direction) and the long axis direction (y-axis direction) of the table top 21 by means of the bearings, guide rail, and linear motion bearing, based on the control signal received from the controlling circuitry 29. Furthermore, the drive apparatus lifts and lowers the table top 21 in a vertical direction (z-axis direction) by means of the bearings, guide rail, and linear motion bearing. In addition, the drive apparatus may rotate the table top 21 by means of the bearings, guide rail, and linear motion bearing, with at least one of the long axis direction and short axis direction serving as the rotation axis so as to incline the table top 21.

The image generating circuitry 23 (image generation function 301 of the processing circuitry 30) creates various images based on the output from the X-ray detector 17. The image generating circuitry 23 outputs the created X-ray images, for example, to the controlling circuitry 29, storage circuitry 31, and display circuitry 33. The image generating circuitry 23 may be realized by processing circuitry, which may be a processor that reads and implements various programs from the storage circuitry 31 so as to realize various image processing operations corresponding to the read-out programs. The above explanation describes various imaging-related functions as being implemented by a single circuit in the processing circuitry. However, multiple independent processors may be combined into processing circuitry so that the various functions may be accomplished by these processors that implement the programs.

The communication interface circuitry 25 is provided with an interfacing function for a network and a not-shown external storage device. The data of various images obtained by the X-ray diagnosis apparatus 1 may be transmitted to other apparatuses via the communication interface circuitry 25 and the network.

The input interface circuitry 27 captures various instructions, commands, information, selection, and settings input from the operator into the X-ray diagnosis apparatus 1. The input interface circuitry 27 may be realized by switches, a mouse, a keyboard, a touch pad having a manipulation surface to be touched to perform an input operation, and a touch panel display in which a display screen and a touch pad are integrated. The input interface circuitry 27 converts the input operation received from the operator to an electric signal. In this specification, the input interface circuitry 27 is not limited to a structure incorporating a mouse, keyboard or any physical operation component. Examples of the input interface circuitry 27 may include processing circuitry that receives an electric signal corresponding to the input operation from an external input device provided separately from the X-ray diagnosis apparatus 1, and outputs the received electric signal to various other circuits.

Specifically, the input interface circuitry 27 inputs X-ray irradiation conditions requested by the operator, including X-ray imaging conditions and X-ray fluoroscoping conditions, fluoroscoping and imaging position, irradiation range, and the position and size of the region of interest in an X-ray image in accordance with the operator's instructions. For instance, the position of the region of interest is not limited to the central portion of the X-ray irradiation range 131, but may be set to any position such as a position off the center of the irradiation range.

The controlling circuitry 29 includes a central processing unit (CPU) and a memory that are not shown. The controlling circuitry 29 realizes various functions by reading various programs for controlling the circuitry and drive apparatus of the X-ray diagnosis apparatus 1 from the storage circuitry 31, and implementing the read-out programs. The controlling circuitry 29 tentatively stores in the memory (not shown in the drawings) the operator's instructions that are transmitted through the input interface circuitry 27, and information including the X-ray irradiation conditions such as imaging and fluoroscoping conditions. The controlling circuitry 29 controls the high voltage generator 11, X-ray diaphragm apparatus 15, drive apparatus, and the like to execute the X-ray imaging and X-ray fluoroscoping (X-ray pulse imaging) in accordance with the operator's instructions, the fluoroscoping and imaging positions, X-ray irradiation conditions, and the like that are stored in the memory.

The controlling circuitry 29 reads a filter control program relating to the X-ray filter control function 291 from the storage circuitry 31 and implements the read-out filter control program, thereby realizing the X-ray filter control function 291. The X-ray filter control function 291 is to control the X-ray filter drive apparatus 153 to move the X-ray filter 151 in accordance with the move of the ROI and a change of the size of the ROI.

The controlling circuitry 29 reads a diaphragm control program relating to the diaphragm control function 293 from the storage circuitry 31, and implements the read-out diaphragm control program, thereby realizing the diaphragm control function 293. The diaphragm control function 293 is to control the blade drive apparatus 157 to move the diaphragm blades 155 so as to match the X-ray irradiation range 131 with the aperture region or partial region 151PR of the X-ray filter 151, or to release the diaphragm blades 155 so as to match with the maximum X-ray irradiation range.

The controlling circuitry 29 reads a program relating to Automatic Brightness Control (hereinafter referred to as an ABC program) from the storage circuitry 31, and implements the read-out ABC program, thereby realizing automatic brightness control function 295. The automatic brightness control is a scheme for obtaining a suitable brightness (hereinafter referred to as a brightness level) in an X-ray image. The automatic brightness control is an active control for maintaining the brightness level within a targeted range, with which, in order to bring the average value or weighted average value of the pixel values in the ROI of an X-ray image of a certain frame closer to the targeted range in the subsequent frame, the X-ray irradiation conditions for the this subsequent frame are changed. The targeted range for the automatic brightness control is not limited to the ROI, and the control may be implemented onto the entire X-ray image. The automatic brightness control may be implemented for the X-ray irradiation range 131 that includes a fluoroscopy target area that is moving, or an area in which the radiation dose considerably changes. The automatic brightness control may not be implemented if subtraction processing is performed. If this is the case, the X-ray irradiation conditions will remain unchanged.

The controlling circuitry 29 reads a determination program relating to a determination function 297 from the storage circuitry 31 and implements the read-out determination program, thereby realizing the determination function 297. The determination function 297 includes determining a transition from a first fluoroscopy (hereinafter referred to as ROI fluoroscopy) in which the fluoroscopy is conducted using the X-ray filter 151 with the diaphragm blades 155 released to the extent of the maximum X-ray irradiation range, to a second fluoroscopy (hereinafter referred to as spot fluoroscopy) in which the fluoroscopy is conducted using the diaphragm blades 155 to limit the X-ray irradiation range 131 to the aperture region or partial region 151PR of the X-ray filter 151; and determining a transition from the spot fluoroscopy to the ROI fluoroscopy. The above functions according to the present embodiment will be discussed later in detail.

In the above explanation, various functions are implemented by a single control circuit in the controlling circuitry 29. The functions, however, may be implemented by combining a plurality of independent processors into the controlling circuitry 29 so that the programs can be implemented by these processors.

Moreover, the processor for each circuitry (unit) of the present embodiment does not always have to be configured as a single circuit, but may be configured as a single processor in which a plurality of independent circuits are combined to implement the functions. In other words, the functions implemented by the controlling circuitry 29 may be implemented by different processing circuits. In addition, the controlling circuitry 29 and image generating circuitry 23 may be integrated into one processor (processing circuitry 30 in FIG. 12) to realize their functions.

The "processor" mentioned above includes, for example, a central processing unit (CPU), graphics processing unit (GPU), and a circuit such as an application specific integrated circuit (ASIC) or programmable logic device (e.g., simple programmable logic device (SPLD), complex programmable logic device (CPLD), and field programmable gate array (FPGA)).

The processor realizes the functions by reading and implementing the programs stored in the storage circuitry 31, which are explained later. Instead of storing the programs in the storage circuitry 31, the programs may be directly loaded in the circuit of the processor. In such a configuration, the processor reads and implements the programs loaded in the circuit to realize the various functions.

Each of the processors according to the present embodiment does not always have to be configured as a single circuit, but a single processor may be provided by combining a plurality of independent circuits to realize their functions. In addition, a plurality of structural components in FIG. 1 may be incorporated into one processor to realize their functions.

The storage circuitry 31 may be composed of various memories such as a hard disk drive (HDD), solid state drive (SSD), magnetic disk (e.g., floppy disk (trademark) and hard disk), optical disk (e.g., CD-ROM and DVD), and a semiconductor memory. The storage circuitry 31 stores X-ray images generated by the image generating circuitry 23, a system control program for the X-ray diagnosis apparatus 1, various image generating programs to be implemented by the image generating circuitry 23, the filter control program, diaphragm control program, ABC program, and determination program to be implemented by the controlling circuitry 29. The storage circuitry 31 further stores a diagnostic protocol, operator's instructions transmitted from the input interface circuitry 27, data sets such as imaging conditions and fluoroscoping conditions relating to the X-ray imaging, and various types of data received through the communication interface circuitry 25 and the network.

The display circuitry 33 corresponds to a display device such as a display or monitor. The display is to show an X-ray image or fluoroscopic image. The display shows a plurality of fluoroscopic images as a moving image in accordance with the imaging frame rate of the ROI fluoroscopy and spot fluoroscopy. The display further shows an input screen for inputting the fluoroscoping and imaging positions and X-ray irradiation conditions.

The overall structure of the X-ray diagnosis apparatus 1 according to the present embodiment has been explained. Next, the details of the present embodiment will be explained. The controlling circuitry 29 of the X-ray diagnosis apparatus 1 according to the present embodiment controls the X-ray diaphragm apparatus 15 in the transition from the ROI fluoroscopy to the spot fluoroscopy in order to shield against the X-rays passing through the X-ray filter 151 outside its aperture region or partial region 151PR. Depending on the positional relationship of the X-ray tube 13, X-ray filter 151 and diaphragm blades 155, the controlling circuitry 29 may control the X-ray diaphragm apparatus 15 in the transition from the ROI fluoroscopy to the spot fluoroscopy in order to shield against the X-rays that are passing through, or have passed through the X-ray filter 151 outside the aperture region or partial region 151PR thereof. If the X-ray filter 151 is arranged on the front surface of the X-ray tube 13, and the diaphragm blades 155 are arranged on the front surface of the X-ray filter 151, the controlling circuitry 29 controls the X-ray diaphragm apparatus 15 to shield against the X-rays that have passed through the X-ray filter 151 outside the aperture region or partial region 151PR in the transition from the ROI fluoroscopy to the spot fluoroscopy. If the diaphragm blades 155 are arranged on the front surface of the X-ray tube 13, and the X-ray filter 151 is arranged on the front surface of the diaphragm blades 155, the controlling circuitry 29 controls the X-ray diaphragm apparatus 15 to shield against the X-rays that are passing through the X-ray filter 151 outside the aperture region or partial region 151PR thereof in the transition from the ROI fluoroscopy to the spot fluoroscopy.

Figure 14:
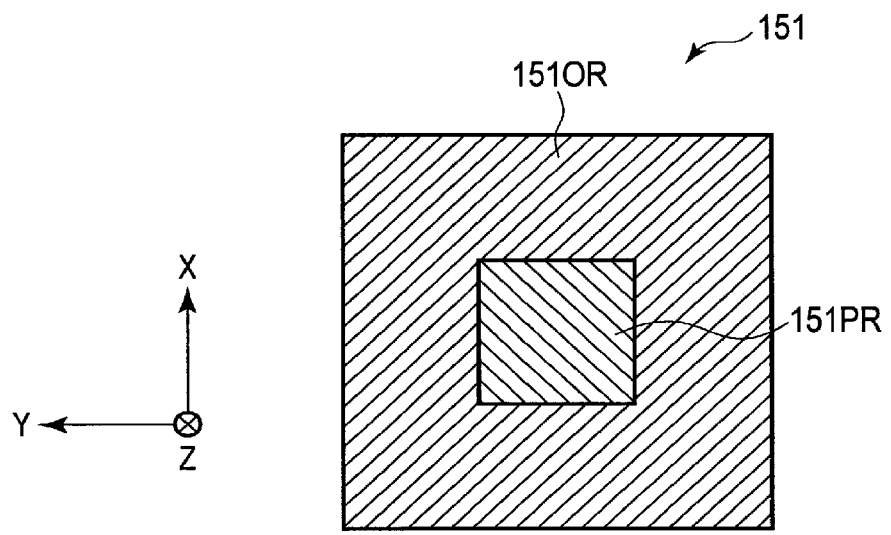
FIG. 14 is a diagram showing the X-ray irradiation range during the ROI fluoroscopy through the different X-ray filter, when viewed from the X-ray irradiation window side according to the present embodiment.

FIGS. 3 and 14 are diagrams of the X-ray irradiation range 131 during the ROI fluoroscopy, when viewed from the side of the X-ray irradiation window 133. The diaphragm blades 155, which are released to the extent of the maximum X-ray irradiation range during the ROI fluoroscopy, are not shown in these drawings. In the X-ray filter 151, the aperture region 152 in FIG. 3 and the partial region 151PR in FIG. 14 are positioned in the central portion of the X-ray irradiation range 131, but their positions are not limited thereto. That is, the aperture region 152 and partial region 151PR may be moved by the X-ray filter drive apparatus 153 in accordance with the position of the ROI of the X-ray filter 151, under the control of the X-ray filter control function 291 of the controlling circuitry 29.

FIG. 4 shows the X-ray irradiation range 131 during the spot fluoroscopy, when viewed from the side of the X-ray irradiation window 133. In this drawing, the aperture region 154 of the diaphragm blades 155 matches the aperture region 152 and partial region 151PR of the X-ray filter 151 during the spot fluoroscopy. That is, in the transition from the ROI fluoroscopy to the spot fluoroscopy, the blade drive apparatus 157 controlled by the diaphragm control function 293 drives the diaphragm blades 155 to reduce the X-ray irradiation range 131 in a manner so that the aperture region 152 or partial region 151PR of the X-ray filter 151 matches the aperture region 154 of the diaphragm blades 155 (arrows 156 in FIG. 4).

The image generating circuitry 23 generates a first fluoroscopic image (hereinafter referred to as a ROI fluoroscopic image) based on the output from the X-ray detector 17 during the ROI fluoroscopy. The image generating circuitry 23 generates a second fluoroscopic image (hereinafter referred to as a spot fluoroscopic image) based on the output from the X-ray detector 17 during the spot fluoroscopy. During the spot fluoroscopy, the image generating circuitry 23 generates a composite image by combining an image of a region that is not the region of interest (hereinafter referred to as a non-ROI image) in the ROI fluoroscopic image and an image of the region of interest (hereinafter referred to as a ROI image) in the spot fluoroscopic image. The non-ROI image corresponds to the irradiation region of X-rays that have passed outside the aperture region or the partial region 151PR. The ROI image corresponds to the irradiation region of the X-rays that have passed through the aperture region or partial region 151PR.

FIG. 5 shows an example of a composite image 231. A region 233 in this drawing corresponds to the ROI in the spot fluoroscopic image, whereas a region 235 in this drawing corresponds to a non-ROI image. The ROI image obtained from the spot fluoroscopy and the non-ROI image obtained from the ROI fluoroscopy are combined into the composite image 231 during the spot fluoroscopy, as illustrated in FIG. 5 and presented on the display.

Figure 6:
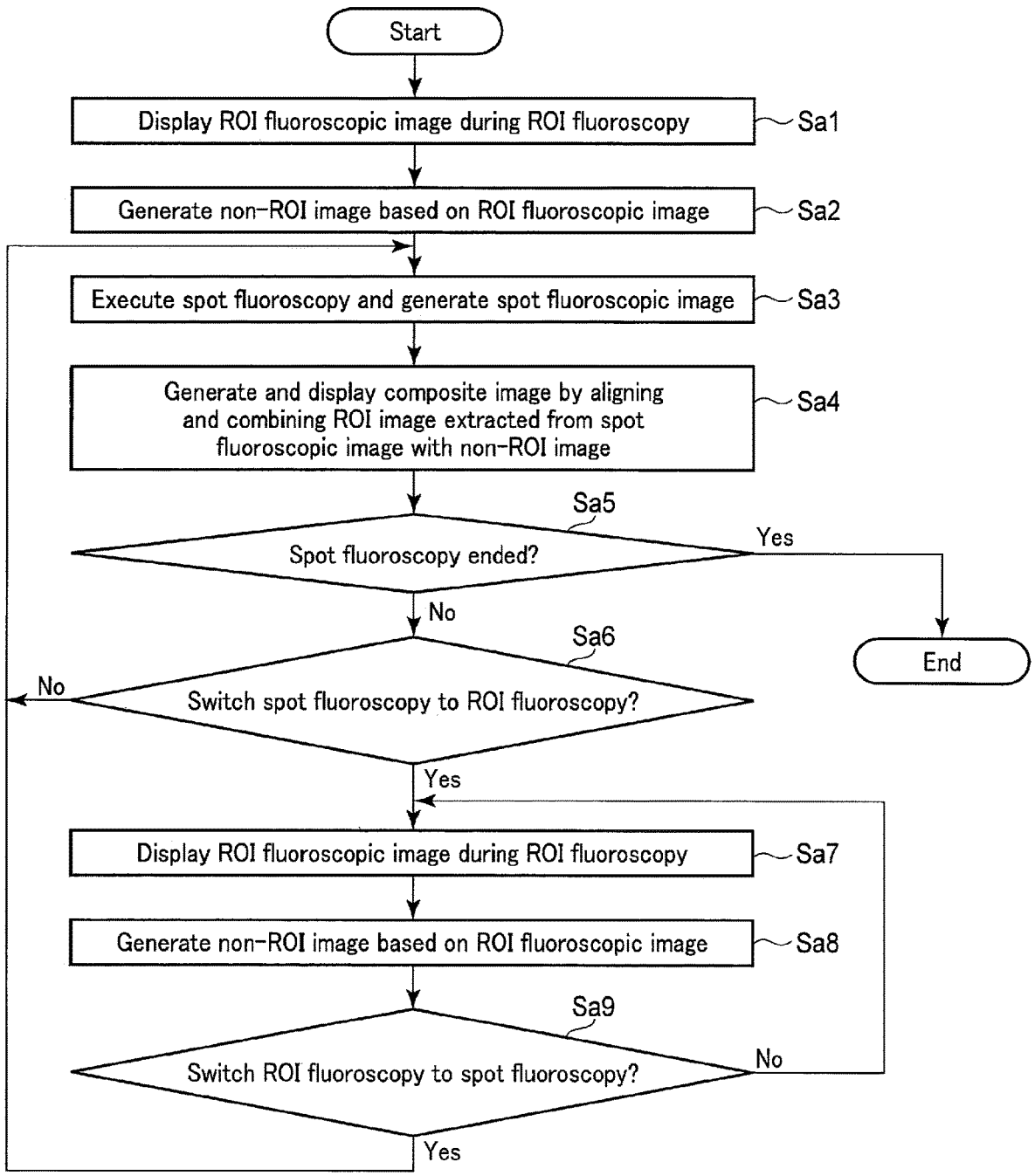
FIG. 6 is a flowchart showing an example of the fluoroscopic processing procedure according to the present embodiment.

FIG. 6 is a flowchart showing an example of the processing procedure of the fluoroscopic function according to the present embodiment. In the following explanation of the flowchart, the X-ray filter 151 having the aperture region 152 will be discussed, as illustrated in FIG. 3. If the X-ray filter 151 having a partial region is to be adopted, the "aperture region 152 of the X-ray filter 151" in the following explanation should be replaced with the "partial region 151PR of the X-ray filter 151".

(Step Sa1)

A region of interest is set in accordance with the operator's instructions received via the input interface circuitry 27. In advance of the ROI fluoroscopy, the controlling circuitry 29 controls the X-ray filter drive apparatus 153 with the X-ray filter control function 291 to match the aperture region 152 of the X-ray filter 151 with the set region of interest. The X-ray filter drive apparatus 153 moves the X-ray filter 151 with the X-ray filter control function 291. As a result, the aperture region 152 of the X-ray filter 151 conforms to the region of interest. Thereafter, the controlling circuitry 29 executes the ROI fluoroscopy in accordance with the predetermined fluoroscopic conditions. The image generating circuitry 23 generates a ROI fluoroscopic image based on the output from the X-ray detector 17. The processing circuitry 30 causes the display to show a ROI fluoroscopic image during the ROI fluoroscopy, with display control function 303. The display circuitry 33 displays the ROI fluoroscopic image.

When the ROI fluoroscopy is repeated, the ROI fluoroscopic images are updated in accordance with the emission of X-ray pulses, and are displayed as a moving image. The ROI fluoroscopy may be performed by one X-ray pulse. In this case, one ROI fluoroscopic image will be displayed. During the ROI fluoroscopy, the automatic brightness control function 295 may be implemented. With the automatic brightness control function 295, the controlling circuitry 29 repeats the ROI fluoroscopy by changing the fluoroscopic conditions until the brightness level in the entire ROI fluoroscopic image or in a partial region of the ROI fluoroscopic image such as the region of interest becomes constant within the targeted range over a predetermined length of time, or in other words, until the brightness values in the ROI fluoroscopic image are stabilized under the automatic brightness control. The predetermined length of time may be set any time before the installation of the apparatus. Alternatively, the predetermined length of time may be set or changed by the user during the operation, or may be automatically set or changed based on the history of the user's operation. That is, the predetermined length of time can be set any time before the implementation of the fluoroscopic function according to the present embodiment.
(Step Sa2)

The image generating circuitry 23 generates a non-ROI image based on the ROI fluoroscopic image. In particular, the image generating circuitry 23 compensates the contrast of pixel values corresponding to the irradiation region (non-ROI) of the X-rays that have passed outside the aperture region in the ROI fluoroscopic image (hereinafter referred to as dose compensation processing), in accordance with the reduction in the X-ray dose by use of the X-ray filter 151, and thereby generates a non-ROI image. In the dose compensation processing, for example, a difference between the pixel values in the fluoroscopy that does not employ the X-ray filter 151 and the pixel values in the fluoroscopy that employs the X-ray filter 151 may be applied to the compensation for the pixel values in the fluoroscopy that employs the X-ray filter 151.

If a plurality of ROI fluoroscopic images are generated in the ROI fluoroscopy, the image generating circuitry 23 may generate a non-ROI image by adding the pixel values of the ROI fluoroscopic images for the same pixel position by use of a recursive filter or any other temporal filter, thereafter averaging the pixel values, and implementing the dose compensation processing onto the averaged pixel value. Furthermore, if the fluoroscopic target area is a heart or any organ that produces motions in specific cycles (e.g., heartbeats), the ROI fluoroscopy may be executed over specific cycles to generate a series of ROI fluoroscopic images in time sequence. Here, the non-ROI image is associated with the time phase (e.g., cardiac phase in an electrocardiogram) in specific cycles and is temporarily stored in the storage circuitry 31.

When the automatic brightness control is implemented onto the ROI fluoroscopy, the image generating circuitry 23 implements the dose compensation processing based on, for example, the ROI fluoroscopic image corresponding to the ROI fluoroscopy performed in accordance with the last updated fluoroscopic conditions, thereby generating a non-ROI image. The non-ROI image is then temporarily stored in the storage circuitry 31.
(Step Sa3)

The controlling circuitry 29 makes a transition from the ROI fluoroscopy to the spot fluoroscopy, based on the determination result obtained from the determination function 297, and executes the spot fluoroscopy. In particular, the controlling circuitry 29 initiates, at a specific timing, controlling the X-ray diaphragm apparatus 15 in the transition period from the ROI fluoroscopy to the spot fluoroscopy, with the diaphragm control function 293 for shielding against the X-rays passing outside the aperture region (non-ROI). The control of the X-ray diaphragm apparatus 15 in the transition period from the ROI fluoroscopy to the spot fluoroscopy is the same as the configuration incorporating the filter illustrated in FIG. 4, and thus the explanation thereof is omitted. The specific timing may be a timing of generating a ROI fluoroscopic image in the ROI fluoroscopy, timing of generating a plurality of ROI fluoroscopic images, or timing of completing the automatic brightness control. That is, in response to the generation of one ROI fluoroscopic image or a plurality of ROI fluoroscopic images, or in response to the completion of the automatic brightness control, the controlling circuitry 29 starts controlling the X-ray diaphragm apparatus 15 during the ROI fluoroscopy.

When the X-ray irradiation range is reduced in a manner in which the aperture region 152 of the X-ray filter 151 matches the aperture region 154 of the diaphragm blades 155, the controlling circuitry 29 executes the spot fluoroscopy. The controlling circuitry 29 may control the high voltage generator 11 in a manner so that the application of a high voltage to the X-ray tube 13 is suspended during the operation of driving the diaphragm blades 155 in the transition period from the ROI fluoroscopy to the spot fluoroscopy. Here, the controlling circuitry 29 may control the display circuitry 33 in a manner in which the ROI fluoroscopic image (first fluoroscopic image) obtained at the latest ROI fluoroscopy (first fluoroscopy) may continue to be displayed. The image generating circuitry 2 generates a spot fluoroscopic image based on the output from the X-ray detector 17.
(Step Sa4)

The image generating circuitry 23 extracts a ROI image from the spot fluoroscopic image. The image generating circuitry 23 aligns and combines the non-ROI image and the ROI image to generate a composite image 231. If the fluoroscopic target is a heart or any organ that produces motions in certain cycles (e.g., heartbeats), the image generating circuitry 23 attaches temporal phase information, such as a cardiac phase based on the electrocardiographic wave, to the ROI image. Here, the image generating circuitry 23 generates a time-series composite image 231 by aligning and combining the ROI image and non-ROI image of the approximately same cardiac phase. During the spot fluoroscopy, the processing circuitry 30 causes the display with the display control function 303 to display this composite image. The display circuitry 33 displays the composite image 231 during the spot fluoroscopy.
(Step Sa5)

When an instruction to terminate the spot fluoroscopy is input through the input interface circuitry 27 (yes in Step Sa5), the processing of the fluoroscopic function according to the present embodiment is ended. If an instruction to terminate the spot fluoroscopy is not input through the input interface circuitry 27 (no in Step Sa5), the process returns to Step Sa6.

(Step Sa6)

The controlling circuitry 29 determines with the determination function 297 as to whether to transition from the spot fluoroscopy to the ROI fluoroscopy. In particular, during the spot fluoroscopy, the controlling circuitry 29 controls the X-ray diaphragm apparatus 15 with the diaphragm control function 293 to transition from the spot fluoroscopy to the ROI fluoroscopy, in accordance with any movement of the table top 21, movement of the support frame 19, movement in the position of the region of interest in the spot image, change in the size of the region of interest, and/or enlargement or reduction of the region of interest (yes in Step Sa6). Upon receipt of an instruction for executing the ROI fluoroscopy that the operator inputs through the input interface circuitry 27 during the spot fluoroscopy, the controlling circuitry 29 may control the X-ray diaphragm apparatus 15 so as to make a transition from the spot fluoroscopy to the ROI fluoroscopy.

To determine whether or not to transition from the spot fluoroscopy to the ROI fluoroscopy, a plurality of predetermined thresholds that correspond to an amount of movement of the table top 21, an amount of movement of the support frame 19, an amount of movement in the position of the region of interest in the spot image, an amount of change in the size of the region of interest, and an amount of enlargement/reduction of the region of interest may be adopted. During the spot fluoroscopy, the controlling circuitry 29 or processing circuitry 30 may compare these amounts with the corresponding thresholds, with the determination function 297. If any of these amounts exceeds the corresponding threshold, the controlling circuitry 29 or processing circuitry 30 controls the X-ray diaphragm apparatus 15 with the diaphragm control function 293 to transition from the spot fluoroscopy to the ROI fluoroscopy. In other words, if none of these amounts exceeds the corresponding threshold during the spot fluoroscopy, the controlling circuitry 29 or processing circuitry 30 would suppress the switching from the spot fluoroscopy to the ROI fluoroscopy. Thus, the robustness in switching from the spot fluoroscopy to the ROI fluoroscopy can be enhanced. The predetermined thresholds may be set any time before the installation of the apparatus. Alternatively, the predetermined thresholds value may be set or changed by the user during the operation, or may be automatically set or changed based on the history of the user's operation. That is, the predetermined thresholds can be set any time before the determination as to whether there is a movement of the table top 21, a movement of the support frame 19, a movement in the position of the region of interest in the spot image, a change of the size of the region of interest, and/or an enlargement/reduction of the region of interest (Step Sa6).

The enlargement of the region of interest is to enlarge the size of the area of the subject P relative to the region of interest that includes the area, by moving the X-ray tube 13 and/or X-ray detector 17 closer to the subject P and thereby shortening the SID. The enlargement of the region of interest may be the enlargement of the region of interest relative to the composite image 231. The reduction of the region of interest is to reduce the size of the area of the subject P relative to the region of interest that includes the area, by moving the X-ray tube 13 and/or X-ray detector 17 further away from the subject P and thereby increasing the SID. The reduction of the region of interest may be the reduction of the region of interest relative to the composite image 231.

Specifically, the controlling circuitry 29 controls the X-ray filter drive apparatus 153 with the X-ray filter control function 291 in order to align the aperture region 152 of the X-ray filter 151 to the position of the region of interest that has been input before executing the ROI fluoroscopy. The X-ray filter drive apparatus 153 moves the X-ray filter 151 under the control of the controlling circuitry 29, as indicated in FIG. 4. The X-ray filter 151 of the aperture region 152 is thereby brought into alignment with the region of interest. The controlling circuitry 29 may control the high voltage generator 11 so as to suspend the high voltage application to the X-ray tube 13 during the operation of driving the diaphragm blades 155 in the transition from the spot fluoroscopy to the ROI fluoroscopy. In this operation, the controlling circuitry 29 may control the display circuitry 33 in a manner so that the spot fluoroscopic image (second fluoroscopic image) that has been obtained from the latest spot fluoroscopy (second fluoroscopy) continues to be displayed.

FIG. 7 is a diagram of the X-ray irradiation range viewed from the side of the X-ray irradiation window 133 after the transition from the spot fluoroscopy to the ROI fluoroscopy. In this drawing, the diaphragm blades 155 are released to the extent of the maximum X-ray irradiation range in the ROI fluoroscopy. That is, during the transition from the spot fluoroscopy to the ROI fluoroscopy, the diaphragm blades 155 are released by the blade drive apparatus 157 to the extent of the maximum X-ray irradiation range (arrows 158 in FIG. 7). With such an operation, the X-rays are irradiated onto the non-ROI as well as to the ROI, and a ROI fluoroscopic image is thereby generated. Based on the ROI fluoroscopic image, a non-ROI image can also be generated.

Figure 8:
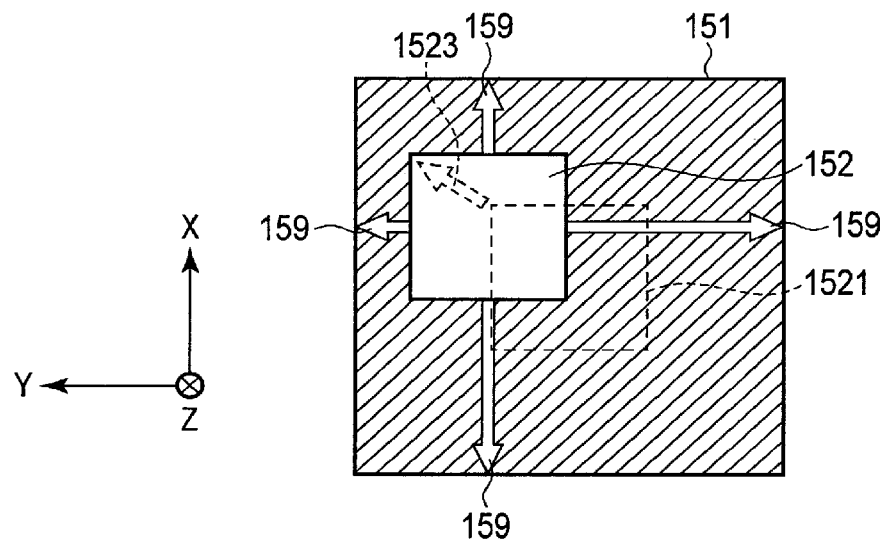
FIG. 8 is a diagram showing an example of a movement of the X-ray filter in accordance with the movement in the position of the region of interest in a spot image and a movement of the diaphragm blades for the transition from the spot fluoroscopy to the ROI fluoroscopy according to the present embodiment.

FIG. 8 is a diagram showing an example of the movement of the X-ray filter 151 in accordance with the movement of the region of interest in the spot image together with the movement of the diaphragm blades 155 for the transition from the spot fluoroscopy to the ROI fluoroscopy. A broken-lined square 1521 in FIG. 8 represents the aperture region 152 of the X-ray filter 151 before the movement in the position of the region of interest. In accordance with the movement in the position of the region of interest, the X-ray filter 151 is moved by the X-ray filter drive apparatus 153 under the control of the X-ray filter control function 291 (arrow 1523 in FIG. 8). In accordance with the movement of the X-ray filter 151, the diaphragm blades 155 are released to the extent of the maximum X-ray irradiation range by the blade drive apparatus 157 under the control of the diaphragm control function 293 (arrows 159 in FIG. 8).

Figure 9:
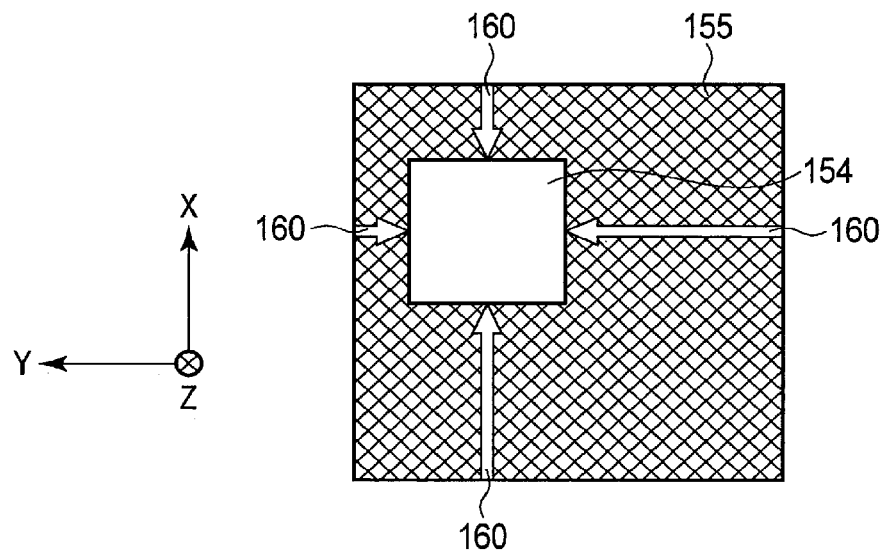
FIG. 9 is a diagram showing the X-ray irradiation range during the spot fluoroscopy after the transition from the ROI fluoroscopy to the spot fluoroscopy in accordance with the movement in the position of the region of interest, when viewed from the X-ray irradiation window side according to the present embodiment.

FIG. 9 is a diagram showing the X-ray irradiation range 131 in the spot fluoroscopy viewed from the side of the X-ray irradiation window 133 after the transition from the ROI fluoroscopy to the spot fluoroscopy in accordance with the movement in the position of the region of interest. In FIG. 9, the aperture region 154 of the diaphragm blades 155 matches the aperture region 152 of the X-ray filter 151 during the spot fluoroscopy. In other words, in the transition from the ROI fluoroscopy to the spot fluoroscopy, the diaphragm blades 155 are driven by the blade drive apparatus 157, which is controlled by the diaphragm control function 293 to reduce the X-ray irradiation range 131 in a manner so that the aperture region 152 of the X-ray filter 151 matches the aperture region 154 of the diaphragm blades 155 (arrows 160 in FIG. 9).

If none of the movement of the table top 21, the movement of the support frame 19, the movement in the position of the region of interest in the spot image, the change of the size of the region of interest, and the enlargement/reduction of the region of interest occurs during the spot fluoroscopy, the controlling circuitry 29 continues the spot fluoroscopy (no in Step Sa6).
(Step Sa7)

The controlling circuitry 29 executes the ROI fluoroscopy. The image generating circuitry 23 generates a ROI fluoroscopic image based on the output from the X-ray detector 17, and the display circuitry 33 displays the ROI fluoroscopic image. The operation in this step is basically the same as Step Sa1, and therefore a detailed explanation is omitted.
(Step Sa8)

The image generating circuitry 23 generates a non-ROI image based on the ROI fluoroscopic image. The operation in this step is basically the same as Step Sa2, and therefore a detailed explanation is omitted. The non-ROI image is updated and temporarily stored in the storage circuitry 31 or the like.
(Step Sa9)

The controlling circuitry 29 determines with the determination function 297 whether to switch from the ROI fluoroscopy to the spot fluoroscopy. Specifically, during the spot fluoroscopy, if any of the movement of the table top 21, the movement of the support frame 19, the movement in the position of the region of interest in the spot image, the change of the size of the region of interest, or the enlargement/reduction of the region of interest occurs, the controlling circuitry 29 continues the ROI fluoroscopy (no in Step Sa9). The controlling circuitry 29 initiates, at a specific timing, to transition from the ROI fluoroscopy to the spot fluoroscopy (yes in Step Sa9) and executes the spot fluoroscopy. The description is provided in Step Sa3, and therefore the detailed explanation is omitted.

If none of the movement of the table top 21, the movement of the support frame 19, the movement in the position of the region of interest in the spot image, the change of the size of the region of interest, and the enlargement/reduction of the region of interest occurs during the ROI fluoroscopy after the transition from the spot fluoroscopy to the ROI fluoroscopy, the controlling circuitry 29 controls the X-ray diaphragm apparatus 15 so as to transition the re-executed ROI fluoroscopy back to the spot fluoroscopy with the diaphragm control function 293 (yes in Step Sa9). For the operation of controlling the X-ray diaphragm apparatus 15 for transitioning from the re-executed ROI fluoroscopy to the spot fluoroscopy, a specific timing may be taken into consideration, as described in Step Sa3.

With the above structure, the following effects may be accomplished:

The X-ray diagnosis apparatus 1 according to the present embodiment controls the X-ray diaphragm apparatus 15 in the transition from the ROI fluoroscopy to the spot fluoroscopy so as to shield against the X-rays passing through the X-ray filter 151 outside the aperture region or partial region; generates a composite image 231 during the spot fluoroscopy by combining a non-ROI image of the ROI fluoroscopic image and a ROI image of the spot fluoroscopic image, the non-ROI image corresponding to an irradiation region of X-rays that have passed outside the aperture region or the partial region, and the ROI image corresponding to an irradiation region of the X-rays that have passed through the aperture region or the partial region; displays the ROI fluoroscopic image during the ROI fluoroscopy; and displays the composite image 231 during the spot fluoroscopy. The combined use of the ROI fluoroscopy and spot fluoroscopy in this manner realizes the reduction in radiation dose to the level close to the dose in the spot fluoroscopy, while realizing the display of an image of the region surrounding the region of interest (i.e., non-ROI image) during the spot fluoroscopy.

According to the present embodiment, a non-ROI image can be generated by dose compensation processing for compensating the contrast of a plurality of pixel values corresponding to the irradiation region of the X-rays that have passed outside the aperture region or partial region in a ROI fluoroscopic image in accordance with the reduction of the X-ray dose (transmissivity) by use of the X-ray filter 151. With such processing, the contrast of the non-ROI in the composite image 231 can be brought closer to the contrast of the ROI in the composite image 231, as a result of which the composite image 231 includes a boundary line of a lowered visibility between the ROI and the non-ROI.

According to the present embodiment, the X-ray diaphragm apparatus 15 can be controlled, in response to the generation of one ROI fluoroscopic image during the ROI fluoroscopy, to transition from the ROI fluoroscopy to the spot fluoroscopy. The time required for carrying out the ROI fluoroscopy thereby can be shortened, which means that the exposure of the subject P to the dose of radiation for the non-ROI can be reduced.

Furthermore, according to the present embodiment, the X-ray diaphragm apparatus 15 can be controlled, in response to the generation of a plurality of ROI fluoroscopic images during the ROI fluoroscopy, to transition from the ROI fluoroscopy to the spot fluoroscopy. A non-ROI image can be generated by averaging the pixel values of these ROI fluoroscopic images with respect to the pixels at the same position of the images. In this manner, the noise in the non-ROI image can be reduced, and a composite image 231 of high quality can be displayed.

According to the present embodiment, the X-ray diaphragm apparatus 15 is controlled, in response to the brightness level of the ROI fluoroscopic image that has stayed constant within the targeted range over a predetermined length of time during the ROI fluoroscopy, to transition from the ROI fluoroscopy to the spot fluoroscopy while controlling the ROI fluoroscopic image obtained in the last ROI fluoroscopy to be displayed. Thus, the ROI fluoroscopy and spot fluoroscopy can be executed under optimum fluoroscopic conditions for displaying the ROI fluoroscopic image and composite image 231, and the ROI fluoroscopic image and composite image 231 can be displayed at optimum brightness levels.

According to the present embodiment, the application of a high voltage to the X-ray tube 13 may be suspended during the operation of moving the diaphragm blades 155 in the transition from the ROI fluoroscopy to the spot fluoroscopy and/or the transition from the spot fluoroscopy to the ROI fluoroscopy. In this manner, during the operation of driving the diaphragm blades 155, the exposure of the subject P to the radiation can be reduced.

According to the present embodiment, the X-ray diaphragm apparatus 15 can be controlled during the spot fluoroscopy to transition from the spot fluoroscopy to the ROI fluoroscopy in accordance with any movement of the table top 21, movement of the support frame 19, movement in the position of the region of interest, a change in the size of the region of interest, and/or enlargement or reduction of the region of interest. In other words, when an operation is initiated in direct or indirect relation to the region of interest in the spot fluoroscopy, the ROI fluoroscopy can be executed to obtain a non-ROI image suitable for the composite image 231. In this manner, a non-ROI image suitable for the composite image 231 displayed during the spot fluoroscopy can be obtained, and a displacement that tends to appear between the ROI image and non-ROI image in the composite image 231 can be suppressed.

Additionally, according to the present embodiment, if none of a movement of the table top 21, movement of the support frame 19, movement in the position of the region of interest, change in the size of the region of interest, and enlargement or reduction of the region of interest occurs during the ROI fluoroscopy after the transition from the spot fluoroscopy to the ROI fluoroscopy, the X-ray diaphragm apparatus 15 can be controlled to transition from the re-executed ROI fluoroscopy to the spot fluoroscopy. In other words, the spot fluoroscopy can be conducted basically when there is no operation in direct or indirect relation to the region of interest. As a result, the time required for carrying out the ROI fluoroscopy can be shortened, which can reduce the exposure of the subject P to the dose of radiation for the non-ROI.

(First Modification)

The difference between the first modification and the above embodiment resides in that when the length of time for executing the spot fluoroscopy reaches a predetermined length, the X-ray diaphragm apparatus 15 is controlled to transition from the spot fluoroscopy to the ROI fluoroscopy. The processing in this modification may be combined with the processing of the above embodiment.

The storage circuitry 31 stores a predetermined length of time. The predetermined length of time may be suitably set in accordance with the fluoroscopy target area, age of the subject P, and the like. The predetermined length may be several minutes. The predetermined length may be set any time before the installation of the apparatus.

Alternatively, the predetermined length may be set or changed by the user during the operation, or may be automatically set or changed based on the history of the user's operation. That is, the predetermined length can be set any time before the determination as to whether the spot fluoroscopy should be switched to the ROI fluoroscopy (Step Sa6).

In the operation in Step Sa6, the controlling circuitry 29 determines, with the determination function 297, whether or not the length of time for executing the spot fluoroscopy reaches a predetermined length. When the length of time for executing the spot fluoroscopy reaches the predetermined length, the controlling circuitry 29 controls the X-ray diaphragm apparatus 15 to transition from the spot fluoroscopy to the ROI fluoroscopy.

With the above control, according to the present modification, even if there is no operation in direct or indirect relation to the region of interest during the spot fluoroscopy, the ROI fluoroscopy can be executed at predetermined intervals. Thus, the non-ROI of the composite image 231 can be updated at predetermined intervals. In other words, according to this modification, even when the subject P moves, the latest non-ROI images can be obtained at predetermined intervals, thereby suppressing any displacement between the ROI image and the non-ROI image in the composite image 231.

(Second Modification)

The difference between this modification and the above embodiment resides in that the X-ray diaphragm apparatus 15 is controlled to transition from the spot fluoroscopy to the ROI fluoroscopy when the pixel value of at least one pixel included in the peripheral portion of the region of interest in the spot fluoroscopic image or composite image 231 has deviated from a predetermined range. The processing in this modification may be combined with the processing of the above embodiment and the first modification.

The storage circuitry 31 stores a predetermined range, which is a range of pixel values defined by the upper and lower limits of the pixel value in the peripheral portion of the ROI in the composite image 231. The upper and lower limits of the pixel value may be set to values that would be affected by any change in the fluoroscopic conditions in accordance with the automatic brightness control or the like. The predetermined range according to this modification may be set any time before the installation of the apparatus. Alternatively, the predetermined range may be set or changed by the user during the operation, or may be automatically set or changed based on the history of the user's operation. That is, the predetermined range can be set any time before the determination as to whether the spot fluoroscopy should be switched to the ROI fluoroscopy (Step Sa6).

In Step Sa6, the controlling circuitry 29 may determine, with the determination function 297, whether or not the pixel value of at least one pixel included in the peripheral portion of the ROI in the spot fluoroscopic image or composite image has deviated from the range of pixel values. What is compared with the range of pixel values may be the average value or median value of pixel values corresponding to a plurality of pixels included in the peripheral portion. The controlling circuitry 29 monitors the pixel values included in the peripheral portion during the spot fluoroscopy, and when the pixel value of at least one pixel included in the peripheral portion has deviated from the range of pixel values, the controlling circuitry 29 controls the X-ray diaphragm apparatus 15 to transition from the spot fluoroscopy to the ROI fluoroscopy.

FIG. 10 is a diagram showing an example of the composite image 231 including a ROI 2311, a peripheral portion 2313 of the ROI 2311, and a non-ROI 2315. In this drawing, the ROI 2311 corresponds to a square shown by the dashed-dotted line. The peripheral portion 2313 of the ROI 2311 corresponds to the shaded area between the dashed-dotted line and dashed line in FIG. 10. The width of the peripheral portion 2313 is predetermined to be any number of pixels.

With the above control according to the present modification, even if there is no operation in direct or indirect relation to the ROI 2311 during the spot fluoroscopy, the X-ray diaphragm apparatus 15 is controlled to transition from the spot fluoroscopy to the ROI fluoroscopy when the pixel value of at least one pixel included in the peripheral portion 2313 of the ROI 2311 in the spot fluoroscopic image or composite image 231 has deviated from a predetermined range. That is, according to the present modification, a non-ROI image can be obtained when a pixel value that is being monitored has deviated from the range of pixel values, and in this manner, the displacement between the ROI image and non-ROI image can be suppressed in the composite image 231.

(Third Modification)

The difference between the third modification and the above embodiment resides in that calculation is performed to find a difference value between the pixel value of at least one pixel included in the peripheral portion 2313 of the ROI 2311 and the pixel value adjacent to the at least one pixel and included in the non-ROI 2315 in the composite image 231, and when the calculated difference value has deviated from the predetermined range, the X-ray diaphragm apparatus 15 is controlled to transition from the spot fluoroscopy to the ROI fluoroscopy. The processing in this modification may be combined with the processing of the above embodiment and the above modifications.

The storage circuitry 31 stores a predetermined range, which is a range of the difference value defined by the upper and lower limits. The upper and lower limits of the difference value may be values that, when the fluoroscopic conditions are changed in accordance with the automatic brightness control or the like, would make the boundary line between the ROI 2311 and the non-ROI 2315 slightly visible in the composite image 231. The predetermined range according to this modification may be set any time before the installation of the apparatus. Alternatively, the predetermined range may be set or changed by the user during the operation, or may be automatically set or changed based on the history of the user's operation. That is, the predetermined range can be set any time before the determination as to whether the spot fluoroscopy should be switched to the ROI fluoroscopy (Step Sa6).

In Step Sa6, the controlling circuitry 29 may calculate the difference value between the pixel value of at least one pixel included in the peripheral portion 2313 of the ROI 2311 and the pixel value of a pixel adjacent to the at least one pixel and included in the non-ROI 2315 in the composite image 231. Thereafter, the controlling circuitry 29 determines, with the determination function 297, whether or not the calculated difference value has deviated from the range of the difference value. What is compared with the range of the difference value may be a difference value between the average value of pixel values corresponding to a plurality of multiple pixels included in the peripheral portion 2313 and the average value of pixel values corresponding to multiple pixels adjacent to the peripheral portion 2313 and included in the peripheral portion of the non-ROI 2315. In place of the average values, median values may be adopted. The controlling circuitry 29 monitors the calculated difference value during the spot fluoroscopy, and if the calculated value has deviated from the range of difference values, the controlling circuitry 29 controls the X-ray diaphragm apparatus 15 to transition from the spot fluoroscopy to the ROI fluoroscopy.

FIG. 11 is a diagram showing an example of the composite image 231 including the ROI 2311, the peripheral portion 2313 of the ROI 2311, and a peripheral portion 2317 of the non-ROI 2315 that is adjacent to the peripheral portion 2313. In this drawing, the ROI 2311 corresponds to a square shown by a dashed-dotted line, and the peripheral portion 2313 of the ROI 2311 corresponds to the area shaded with dots. The peripheral portion 2317 included in the non-ROI 2315 corresponds to the slashed area in FIG. 11. The widths of the peripheral portions 2313 and 2317 are predetermined to be any number of pixels.

With the above control, according to the present modification, even if there is no operation in direct or indirect relation to the ROI 2311 of the spot fluoroscopy, a difference value between the pixel value of at least one pixel included in the peripheral portion 2313 in the ROI 2311 and the pixel value of the pixel adjacent to the at least one pixel and included in the non-ROI 2315 in the composite image 231 is calculated, and when the calculated difference value has deviated from the range of difference values, the X-ray diaphragm apparatus 15 is controlled to transition from the spot fluoroscopy to the ROI fluoroscopy. According to the present modification, when the calculated difference value has deviated from the range of the difference value, a non-ROI image can be obtained. Thus, in the composite image 231, a displacement between the ROI image and the non-ROI image can be suppressed.

(Application Example)

According to the application example, the fluoroscopic function is applied to the distal end of a catheter inserted into the subject P.

The controlling circuitry 29 detects the distal end of the catheter in a ROI fluoroscopic image generated from the ROI fluoroscopy. Specifically, the controlling circuitry 29 identifies the distal end of the catheter in the ROI fluoroscopic image by performing an edge detection process or the like onto the ROI fluoroscopic image. The controlling circuitry 29 determines the position of the aperture region in the X-ray filter 151 in a manner so that the ROI fluoroscopic image would include the distal end of the catheter. The controlling circuitry 29 controls the X-ray filter drive apparatus 153 in accordance with the position of the region of interest in the ROI fluoroscopic image to match the aperture region 152 of the X-ray filter 151 to the region of interest.

The controlling circuitry 29 determines, with the determination function 297, whether or not the distal end of the catheter has been moved in the ROI fluoroscopic image. The controlling circuitry 29 may determine the movement of the distal end of the catheter, for example, by subtracting the ROI fluoroscopic image generated immediately before from the current ROI fluoroscopic image. When detecting the movement of the distal end of the catheter, the controlling circuitry 29 sets the region of interest in a manner so that the ROI fluoroscopic image includes the distal end of the catheter. As described above, the controlling circuitry 29 controls the X-ray filter drive apparatus 153 in accordance with the position of the region of interest that includes the distal end of the catheter, so as to match the aperture region 152 of the X-ray filter 151 to the region of interest. When the movement of the distal end of the catheter is being detected in the ROI fluoroscopic image, or in other words when the distal end of the catheter is being moved, the controlling circuitry 29 executes the ROI fluoroscopy while moving the region of interest to follow the distal end of the catheter.

When the distal end of the catheter has moved and is positioned near the edge portion of the ROI fluoroscopic image, the controlling circuitry 29 may control the drive apparatus based on the traveling direction and traveled distance of the distal end of the catheter to move the support frame 19 and/or the table top 21. In this manner, according to the application example, the ROI fluoroscopic image can be generated to follow the movement of the distal end of the catheter. The controlling circuitry 29 may also fix the region of interest at the center of the ROI fluoroscopic image, and control the movement of the support frame 19 and/or table top 21 to follow the distal end of the moving catheter in a manner so that the region of interest always contains the distal end of the catheter.

In response to the detection of no movement of the distal end of the catheter, or in other words in response to the suspension of the movement of the distal end of the catheter in the ROI fluoroscopic image, the controlling circuitry 29 controls the X-ray diaphragm apparatus 15 to transition from the ROI fluoroscopy to the spot fluoroscopy. The controlling circuitry 29 identifies the distal end of the catheter in the composite image 231 by performing an edge detection process or the like onto the composite image 231 generated during the spot fluoroscopy. The controlling circuitry 29 determines, with the determination function 297, whether or not the distal end of the catheter has been moved during the spot fluoroscopy. The controlling circuitry 29 may subtract, for example, the composite image generated immediately before from the current composite image 231 to determine whether the distal end of the catheter has been moved. When the movement of the distal end of the catheter is detected during the spot fluoroscopy, the controlling circuitry 29 controls the X-ray diaphragm apparatus 15 to transition from the spot fluoroscopy to the ROI fluoroscopy. When no movement of the distal end of the catheter is detected in the composite image 231, or in other words, when the distal end of the catheter is stopped, the controlling circuitry 29 executes the spot fluoroscopy.

The above process is repeated until the fluoroscopic function is terminated according to the present embodiment. For the transition from the ROI fluoroscopy to the spot fluoroscopy and the transition from the spot fluoroscopy to the ROI fluoroscopy, the processes in the above embodiment and modifications may be adopted in combination.

With the above control, according to the present application example, the position of the aperture region can be determined by detecting the distal end of the catheter in a ROI fluoroscopic image in a manner so that the ROI fluoroscopic image would include the distal end of the catheter, and in response to the detection of the movement of the distal end of the catheter, the X-ray diaphragm apparatus 15 is controlled to transition from the spot fluoroscopy to the ROI fluoroscopy; the ROI fluoroscopy is executed during the movement of the distal end of the catheter; in response to the detection of no movement of the distal end of the catheter, the X-ray diaphragm apparatus 15 is controlled to transition from the ROI fluoroscopy to the spot fluoroscopy; and the spot fluoroscopy is executed during a period of the distal end of the catheter not being moved. According to the present application example, the region of interest can be determined in a manner to follow the distal end of the catheter, and the ROI fluoroscopy and the spot fluoroscopy can be switched in accordance with a movement or no movement of the distal end of the catheter.

The X-ray diagnosis apparatus 1 according to the present embodiment, modifications, and application example can display an image of the ROI surrounding portion while reducing the dose of radiation corresponding to the spot fluoroscopy when executing the spot fluoroscopy.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnosis apparatus, comprising:
an X-ray detector which is arranged to face an X-ray tube that generates X-rays and detects the X-rays;
an X-ray diaphragm apparatus which includes diaphragm blades shielding against the X-rays and an X-ray filter including an aperture region or a partial region having a higher X-ray transmissivity than a remaining region of the X-ray filter; and
processing circuitry configured:
to control the X-ray diaphragm apparatus during a transition from first fluoroscopy employing the X-ray filter to second fluoroscopy employing the diaphragm blades to restrict an irradiation range in such a manner as to shield, at implementation of the second fluoroscopy, the X-rays that pass through the X-ray filter outside the aperture region or the partial region at implementation of the first fluoroscopy,
to generate a plurality of first fluoroscopic images based on an output from the X-ray detector during the first fluoroscopy,
to generate a second fluoroscopic image based on an output from the X-ray detector during the second fluoroscopy,
to generate a composite image during the second fluoroscopy, by combining a non-region-of-interest image of the plurality of first fluoroscopic images and a region-of-interest image of the second fluoroscopic image, the non-region-of-interest image corresponding to an irradiation region of X-rays that have passed outside the aperture region or the partial region, and the region-of-interest image corresponding to an irradiation region of the X-rays that have passed through the aperture region or the partial region,
to display the plurality of first fluoroscopic images on a display during the first fluoroscopy, and
to display the composite image on the display during the second fluoroscopy,
wherein the processing circuitry switches from first fluoroscopy to second fluoroscopy by controlling the X-ray diaphragm apparatus in response to generation of the plurality of the first fluoroscopic images during the first fluoroscopy,
the processing circuitry generates the non-region-of-interest image in which noise is reduced by averaging pixel values of the plurality of first fluoroscopic images at same pixel positions, and
wherein the processing circuitry is further configured:
to detect a distal end of a catheter in the first fluoroscopic image and thereby determine a position of the aperture region or the partial region in a manner to include the distal end,
to control the X-ray diaphragm apparatus to transition from the second fluoroscopy to the first fluoroscopy in response to a detection of a movement of the distal end,
to execute the first fluoroscopy during the movement of the distal end,
to control the X-ray diaphragm apparatus to transition from the first fluoroscopy to the second fluoroscopy in response to no movement of the distal end, and
to execute the second fluoroscopy when no movement of the distal end is detected.

2. The X-ray diagnosis apparatus according to claim 1, wherein the processing circuitry is configured to generate the non-region-of-interest image by compensating a contrast of a plurality of pixel values corresponding to the irradiation region of the X-rays that have passed outside the aperture region or the partial region in the first fluoroscopic image, in accordance with a reduction in radiation dose by use of the X-ray filter.

3. The X-ray diagnosis apparatus according to claim 1, wherein
the processing circuitry is configured to control the X-ray diaphragm apparatus in response to a brightness level of the first fluoroscopic image that has stayed within a target range for a predetermined length of time during the first fluoroscopy.

4. The X-ray diagnosis apparatus according to claim 1, wherein the processing circuitry is configured:
to suspend application of a high voltage to the X-ray tube when the diaphragm blades are being driven during the transition from the first fluoroscopy to the second fluoroscopy, and to continue to display the first fluoroscopic image that has been obtained in the first fluoroscopy executed immediately before.

5. The X-ray diagnosis apparatus according to claim 1, the apparatus further comprising:
 a bed that movably supports a table top on which a subject is positioned, and
 a support frame that movably supports the X-ray tube and the X-ray detector,
 wherein the processing circuitry is configured to control the X-ray diaphragm apparatus to transition from the second fluoroscopy to the first fluoroscopy if a movement of the table top, a movement of the support frame, a movement of a position of a region of interest, a change in size of the region of interest, and/or enlargement/reduction of the region of interest occurs during the second fluoroscopy.

6. The X-ray diagnosis apparatus according to claim 1, wherein
 when a length of time for executing the second fluoroscopy reaches a predetermined length of time, the processing circuitry is configured to control the X-ray diaphragm apparatus to transition from the second fluoroscopy to the first fluoroscopy.

7. The X-ray diagnosis apparatus according to claim 1, wherein
 the processing circuitry is configured to control the X-ray diaphragm apparatus to transition from the second fluoroscopy to the first fluoroscopy when a pixel value of at least one pixel included in a peripheral portion of the region of interest in the second fluoroscopic image or the composite image has deviated from a predetermined range.

8. The X-ray diagnosis apparatus according to claim 1, wherein the processing circuitry is configured:
 to calculate a difference value between a pixel value of at least one pixel included in a peripheral portion of the region-of-interest image in the composite image and a pixel value of a pixel adjacent to the at least one pixel and included in the non-region-of-interest image,
 to control the X-ray diaphragm apparatus to transition from the second fluoroscopy to the first fluoroscopy when the difference value has deviated from a predetermined range.

9. The X-ray diagnosis apparatus according to claim 1, wherein
 the aperture region or the partial region is positioned off a center of the first fluoroscopic image.

10. The X-ray diagnosis apparatus according to claim 5, wherein
 the processing circuitry is configured to control the X-ray diaphragm apparatus to transition from the re-executed first fluoroscopy to the second fluoroscopy if none of the movement of the table top, the movement of the support frame, the change in a position of a region of interest, the change in size of the region of interest, and the enlargement/reduction of the region of interest occurs during the first fluoroscopy after the transition from the second fluoroscopy to the first fluoroscopy.

11. The X-ray diagnosis apparatus according to claim 10, wherein
 the processing circuitry is configured to suspend application of a high voltage to the X-ray tube when the diaphragm blades are being driven during the transition from the second fluoroscopy to the first fluoroscopy.

* * * * *